(12) United States Patent
Byass et al.

(10) Patent No.: US 6,797,690 B1
(45) Date of Patent: Sep. 28, 2004

(54) CARROT ANTIFREEZE POLYPEPTIDES

(75) Inventors: Louise Jane Byass, Alberta (CA); Charlotte Juliette Doucet, York (GB); Richard Anthony Fenn, Bedford (GB); Andrew John McArthur, Bedford (GB); Christopher Michael Sidebottom, Bedford (GB); Margaret Felicia Smallwood, York (GB)

(73) Assignee: Good Humor — Breyers Ice Cream, division of Conopco, Inc., Green Bay, WI (US)

( * ) Notice: Subject to any disclaimer, the term of this patent is extended or adjusted under 35 U.S.C. 154(b) by 0 days.

(21) Appl. No.: 09/308,140

(22) PCT Filed: Nov. 6, 1997

(86) PCT No.: PCT/EP97/06181

§ 371 (c)(1),
(2), (4) Date: Dec. 30, 1990

(87) PCT Pub. No.: WO98/22591

PCT Pub. Date: May 28, 1998

(30) Foreign Application Priority Data

Nov. 19, 1996 (EP) .............................. 96308362

(51) Int. Cl.$^7$ .......................... A61K 38/16; A23B 7/00; A23G 9/00
(52) U.S. Cl. .............................. 514/2; 514/12; 530/350; 530/326; 530/325; 530/300; 426/100; 426/49; 426/565; 426/660
(58) Field of Search ....................... 514/2, 12; 530/350, 530/326, 328, 300; 426/100, 49, 565, 660; 435/7.1, 6

(56) References Cited

U.S. PATENT DOCUMENTS 5,118,792 A 6/1992 Warren et al.
5,928,877 A * 7/1999 Lance et al. ................. 435/7.1
6,096,867 A 8/2000 Byass et al.

FOREIGN PATENT DOCUMENTS

| WO | 90/13571 | 11/1990 |
|----|----------|---------|
| WO | 91/08292 | 6/1991 |
| WO | 92/22581 | 12/1992 |
| WO | 94/03617 | 2/1994 |
| WO | 94/17186 | 8/1994 |
| WO | 96/11586 | 4/1996 |
| WO | 98/04148 | 2/1998 |

OTHER PUBLICATIONS

International Search Report dated May 28, 1998.

European Search Report dated May 22, 1997.

Duman et al., *Thermal Hysteresis Protein Activity in Bacteria Fungi and Phylogenetically Diverse Plants*, Cryobiology 30 (3), 1993, pp. 322–328.

Lee et al., *The Reduction of the Freezing Point of Tobacco Plants Transformed eith the Gene Encoding for the Antifreeze Protein from Winter Flounder*, J. Cell Biochem. Suppl., vol. 14E, 1990, p. 303.

\* cited by examiner

Primary Examiner—Karen Cochrane Carlson
Assistant Examiner—Samuel Wei Liu
(74) Attorney, Agent, or Firm—Gerard J. McGowan, Jr.

(57) ABSTRACT

Novel antifreeze polypeptides which can be easily obtained from an abundant natural source. Antifreeze polypeptides obtained from carrots show markedly better properties as compared to polypeptides obtained from other vegetables. The antifreeze polypeptides of the invention are capable of providing good recrystallization inhibition properties without significantly changing the crystal shape of the ice-crystals, therewith possibly leading to more favorable properties, e.g., soft ice-cream.

16 Claims, No Drawings

SEQUENCE LISTING

```
<160> NUMBER OF SEQ ID NOS: 12

<210> SEQ ID NO 1
<211> LENGTH: 7
<212> TYPE: PRT
<213> ORGANISM: Daucus carota

<400> SEQUENCE: 1

Leu Pro Asn Leu Phe Gly Lys
 1               5

<210> SEQ ID NO 2
<211> LENGTH: 9
<212> TYPE: PRT
<213> ORGANISM: Daucus carota

<400> SEQUENCE: 2

Ile Pro Glu Glu Ile Ser Ala Leu Lys
 1               5

<210> SEQ ID NO 3
<211> LENGTH: 10
<212> TYPE: PRT
<213> ORGANISM: Daucus carota
<220> FEATURE:
<221> NAME/KEY: MOD_RES
<222> LOCATION: (3)
<223> OTHER INFORMATION: any, other or unknown amino acid

<400> SEQUENCE: 3

Leu Thr Xaa Leu Asp Leu Ser Phe Asn Lys
 1               5                  10

<210> SEQ ID NO 4
<211> LENGTH: 22
<212> TYPE: PRT
<213> ORGANISM: Daucus carota
<220> FEATURE:
<221> NAME/KEY: MOD_RES
<222> LOCATION: (21)
<223> OTHER INFORMATION: any, other or unknown amino acid

<400> SEQUENCE: 4

Ser Leu Arg Leu Ser Ser Thr Ser Leu Ser Gly Pro Val Pro Leu Phe
 1               5                  10                  15

Phe Pro Gln Leu Xaa Lys
             20

<210> SEQ ID NO 5
<211> LENGTH: 16
<212> TYPE: PRT
<213> ORGANISM: Daucus carota
<220> FEATURE:
<221> NAME/KEY: MOD_RES
<222> LOCATION: (1)..(16)
<223> OTHER INFORMATION: Xaa represents any, other or unknown amino
      acid
```

<400> SEQUENCE: 5

Xaa Xaa Glu Val Ile Pro Xaa Gln Leu Ser Thr Leu Pro Asn Leu Lys
 1               5                  10                  15

<210> SEQ ID NO 6
<211> LENGTH: 999
<212> TYPE: DNA
<213> ORGANISM: Daucus carota
<220> FEATURE:
<221> NAME/KEY: CDS
<222> LOCATION: (1)..(996)

<400> SEQUENCE: 6

| atg aat att gaa tca tct ttc tgc cct att ttg tgc ata tgc atg att | 48 |
| Met Asn Ile Glu Ser Ser Phe Cys Pro Ile Leu Cys Ile Cys Met Ile |  |
|  1               5                  10                  15 |  |

| ttc ctc tgc ctt cca aac ctc tct gca tca caa aga tgc aac aac aac | 96 |
| Phe Leu Cys Leu Pro Asn Leu Ser Ala Ser Gln Arg Cys Asn Asn Asn |  |
|                 20                  25                  30 |  |

| gac aag caa gct tta ctc caa atc aaa aca gcc ttg aaa aac ccc acc | 144 |
| Asp Lys Gln Ala Leu Leu Gln Ile Lys Thr Ala Leu Lys Asn Pro Thr |  |
|             35                  40                  45 |  |

| att aca gac tca tgg gtg tca gac gac gat tgt tgt ggt tgg gac cta | 192 |
| Ile Thr Asp Ser Trp Val Ser Asp Asp Asp Cys Cys Gly Trp Asp Leu |  |
|         50                  55                  60 |  |

| gtc gaa tgt gac gaa acc agc aac cgc ata att tcc ctc ata att caa | 240 |
| Val Glu Cys Asp Glu Thr Ser Asn Arg Ile Ile Ser Leu Ile Ile Gln |  |
|     65                  70                  75                  80 |  |

| gac gac gaa gct ctc acc ggc caa atc cca cct cag gtg gga gac cta | 288 |
| Asp Asp Glu Ala Leu Thr Gly Gln Ile Pro Pro Gln Val Gly Asp Leu |  |
|                     85                  90                  95 |  |

| cca tac ctc caa gcc tta tgg ttc cgt aaa ctc ccc aat ctt ttc gga | 336 |
| Pro Tyr Leu Gln Ala Leu Trp Phe Arg Lys Leu Pro Asn Leu Phe Gly |  |
|                 100                 105                 110 |  |

| aaa atc cca gaa gaa att tct gca ctc aaa gac cta aaa tcc ctc aga | 384 |
| Lys Ile Pro Glu Glu Ile Ser Ala Leu Lys Asp Leu Lys Ser Leu Arg |  |
|             115                 120                 125 |  |

| ctc agc tcg acc agt ctc agt ggc cct gtc cct tta ttc ttc cct cag | 432 |
| Leu Ser Ser Thr Ser Leu Ser Gly Pro Val Pro Leu Phe Phe Pro Gln |  |
|         130                 135                 140 |  |

| ctt acg aaa cta act tgt tta gac tta tcg ttt aac aaa ctt ttg ggt | 480 |
| Leu Thr Lys Leu Thr Cys Leu Asp Leu Ser Phe Asn Lys Leu Leu Gly |  |
| 145                 150                 155                 160 |  |

| gta atc cct cct cag ctt tcc act ctt ccg aac ctt aaa gcc ctg cac | 528 |
| Val Ile Pro Pro Gln Leu Ser Thr Leu Pro Asn Leu Lys Ala Leu His |  |
|                     165                 170                 175 |  |

| tta gaa cgt aac gaa ctc acc ggt gaa atc ccc gat atc ttt ggg aat | 576 |
| Leu Glu Arg Asn Glu Leu Thr Gly Glu Ile Pro Asp Ile Phe Gly Asn |  |
|                 180                 185                 190 |  |

| ttt gct gga tcc ccg gac ata tat ctt tcg cat aac cag ctc acc ggg | 624 |
| Phe Ala Gly Ser Pro Asp Ile Tyr Leu Ser His Asn Gln Leu Thr Gly |  |
|             195                 200                 205 |  |

| ttt gtt ccc aaa act ttt gct aga gca gat cca att agg ctc gac ttc | 672 |
| Phe Val Pro Lys Thr Phe Ala Arg Ala Asp Pro Ile Arg Leu Asp Phe |  |
|         210                 215                 220 |  |

| tca ggg aac aga cta gaa ggt gat att tca ttc ttg ttt ggg cct aaa | 720 |
| Ser Gly Asn Arg Leu Glu Gly Asp Ile Ser Phe Leu Phe Gly Pro Lys |  |
| 225                 230                 235                 240 |  |

| aaa cgc ttg gaa atg cta gat ttt tca gga aac gtg ctt agt ttc aat | 768 |
| Lys Arg Leu Glu Met Leu Asp Phe Ser Gly Asn Val Leu Ser Phe Asn |  |

```
                    245                 250                 255
ttc tcc agg gtg cag gag ttt cca ccc tct ttg aca tac tta gac ttg      816
Phe Ser Arg Val Gln Glu Phe Pro Pro Ser Leu Thr Tyr Leu Asp Leu
            260                 265                 270 aac cat aac cag atc agc gga agt ctg tcg agt gaa ttg gct aaa ttg      864
Asn His Asn Gln Ile Ser Gly Ser Leu Ser Ser Glu Leu Ala Lys Leu
        275                 280                 285 gac ctg cag aca ttt aac gtc agt gat aat aat ctc tgc ggc aag att      912
Asp Leu Gln Thr Phe Asn Val Ser Asp Asn Asn Leu Cys Gly Lys Ile
    290                 295                 300 cca aca ggg gga aac ctc cag aga ttc gac cgt acg gcc tat ctc cac      960
Pro Thr Gly Gly Asn Leu Gln Arg Phe Asp Arg Thr Ala Tyr Leu His
305                 310                 315                 320 aac agt tgc ttg tgt ggt gct cca ttg cca gaa tgc tag                  999
Asn Ser Cys Leu Cys Gly Ala Pro Leu Pro Glu Cys
                325                 330
```

<210> SEQ ID NO 7
<211> LENGTH: 332
<212> TYPE: PRT
<213> ORGANISM: Daucus carota

<400> SEQUENCE: 7

```
Met Asn Ile Glu Ser Ser Phe Cys Pro Ile Leu Cys Ile Cys Met Ile
 1               5                  10                  15

Phe Leu Cys Leu Pro Asn Leu Ser Ala Ser Gln Arg Cys Asn Asn Asn
            20                  25                  30

Asp Lys Gln Ala Leu Leu Gln Ile Lys Thr Ala Leu Lys Asn Pro Thr
        35                  40                  45

Ile Thr Asp Ser Trp Val Ser Asp Asp Cys Cys Gly Trp Asp Leu
    50                  55                  60

Val Glu Cys Asp Glu Thr Ser Asn Arg Ile Ile Ser Leu Ile Ile Gln
65                  70                  75                  80

Asp Asp Glu Ala Leu Thr Gly Gln Ile Pro Pro Gln Val Gly Asp Leu
                85                  90                  95

Pro Tyr Leu Gln Ala Leu Trp Phe Arg Lys Leu Pro Asn Leu Phe Gly
            100                 105                 110

Lys Ile Pro Glu Glu Ile Ser Ala Leu Lys Asp Leu Lys Ser Leu Arg
        115                 120                 125

Leu Ser Ser Thr Ser Leu Ser Gly Pro Val Pro Leu Phe Phe Pro Gln
    130                 135                 140

Leu Thr Lys Leu Thr Cys Leu Asp Leu Ser Phe Asn Lys Leu Leu Gly
145                 150                 155                 160

Val Ile Pro Pro Gln Leu Ser Thr Leu Pro Asn Leu Lys Ala Leu His
                165                 170                 175

Leu Glu Arg Asn Glu Leu Thr Gly Glu Ile Pro Asp Ile Phe Gly Asn
            180                 185                 190

Phe Ala Gly Ser Pro Asp Ile Tyr Leu Ser His Asn Gln Leu Thr Gly
        195                 200                 205

Phe Val Pro Lys Thr Phe Ala Arg Ala Asp Pro Ile Arg Leu Asp Phe
    210                 215                 220

Ser Gly Asn Arg Leu Glu Gly Asp Ile Ser Phe Leu Phe Gly Pro Lys
225                 230                 235                 240

Lys Arg Leu Glu Met Leu Asp Phe Ser Gly Asn Val Leu Ser Phe Asn
                245                 250                 255

Phe Ser Arg Val Gln Glu Phe Pro Pro Ser Leu Thr Tyr Leu Asp Leu
```

```
                    260              265              270
Asn His Asn Gln Ile Ser Gly Ser Leu Ser Glu Leu Ala Lys Leu
            275              280              285

Asp Leu Gln Thr Phe Asn Val Ser Asp Asn Asn Leu Cys Gly Lys Ile
        290              295              300

Pro Thr Gly Gly Asn Leu Gln Arg Phe Asp Arg Thr Ala Tyr Leu His
305              310              315              320

Asn Ser Cys Leu Cys Gly Ala Pro Leu Pro Glu Cys
                325              330

<210> SEQ ID NO 8
<211> LENGTH: 8
<212> TYPE: PRT
<213> ORGANISM: Daucus carota

<400> SEQUENCE: 8

Gly Pro Val Pro Leu Phe Phe Pro
 1               5

<210> SEQ ID NO 9
<211> LENGTH: 23
<212> TYPE: DNA
<213> ORGANISM: Daucus carota
<220> FEATURE:
<221> NAME/KEY: modified_base
<222> LOCATION: (1)..(23)
<223> OTHER INFORMATION: "n" represents inosine

<400> SEQUENCE: 9
ggnccngtnc cnytnttytt ycc                                          23

<210> SEQ ID NO 10
<211> LENGTH: 32
<212> TYPE: DNA
<213> ORGANISM: Daucus carota

<400> SEQUENCE: 10
gagagaggat cctcgagttt tttttttttt tt                                32

<210> SEQ ID NO 11
<211> LENGTH: 829
<212> TYPE: DNA
<213> ORGANISM: Daucus carota
<220> FEATURE:
<221> NAME/KEY: CDS
<222> LOCATION: (1)..(591)

<400> SEQUENCE: 11 ggg ccg gtg ccg ctg ttc ttc cct cag ctt acg aaa cta act tgt tta    48
Gly Pro Val Pro Leu Phe Phe Pro Gln Leu Thr Lys Leu Thr Cys Leu
 1               5                  10                  15 gac tta tcg ttt aac aaa ctt ttg ggt gta atc cct cct cag ctt tcc    96
Asp Leu Ser Phe Asn Lys Leu Leu Gly Val Ile Pro Pro Gln Leu Ser
            20                  25                  30 act ctt ccg aac ctt aaa gcc ctg cac tta gaa cgt aac gaa ctc acc   144
Thr Leu Pro Asn Leu Lys Ala Leu His Leu Glu Arg Asn Glu Leu Thr
        35                  40                  45 ggt gaa atc ccc gat atc ttt ggg aat ttt gct gga tcc ccg gac ata   192
Gly Glu Ile Pro Asp Ile Phe Gly Asn Phe Ala Gly Ser Pro Asp Ile
    50                  55                  60 tat ctt tcg cat aac cag ctc acc ggg ttt gtt ccc aaa act ttt gct   240
Tyr Leu Ser His Asn Gln Leu Thr Gly Phe Val Pro Lys Thr Phe Ala
65                  70                  75                  80
```

```
aga gca gat cca att agg ctc gac ttc tca ggg aac aga cta gaa ggt       288
Arg Ala Asp Pro Ile Arg Leu Asp Phe Ser Gly Asn Arg Leu Glu Gly
                 85                  90                  95 gat att tca ttc ttg ttt ggg cct aaa aaa cgc ttg gaa atg cta gat       336
Asp Ile Ser Phe Leu Phe Gly Pro Lys Lys Arg Leu Glu Met Leu Asp
            100                 105                 110 ttt tca gga aac gtg ctt agt ttc aat ttc tcc agg gtg cag gag ttt       384
Phe Ser Gly Asn Val Leu Ser Phe Asn Phe Ser Arg Val Gln Glu Phe
        115                 120                 125 cca ccc tct ttg aca tac tta gac ttg aac cat aac cag atc agc gga       432
Pro Pro Ser Leu Thr Tyr Leu Asp Leu Asn His Asn Gln Ile Ser Gly
    130                 135                 140 agt ctg tcg agt gaa ttg gct aaa ttg gac ctg cag aca ttt aac gtc       480
Ser Leu Ser Ser Glu Leu Ala Lys Leu Asp Leu Gln Thr Phe Asn Val
145                 150                 155                 160 agt gat aat aat ctc tgc ggc aag att cca aca ggg gga aac ctc cag       528
Ser Asp Asn Asn Leu Cys Gly Lys Ile Pro Thr Gly Gly Asn Leu Gln
                165                 170                 175 aga ttc gac cgt acg gcc tat ctc cac aac agt tgc ttg tgt ggt gct       576
Arg Phe Asp Arg Thr Ala Tyr Leu His Asn Ser Cys Leu Cys Gly Ala
            180                 185                 190 cca ttg cca gaa tgc tagttaccat gcaaaatgtg ccttaaggtt atctttgtaa       631
Pro Leu Pro Glu Cys
        195 tgagatatat tatgcagctc aaggcagagc aataagtttt cctaatttgt tatagtaaga    691 tattattgta tttcacagaa agtgtctact aggattcgta atatattata attgctcata    751 attgtatctg tttaatctgt aatccaaaaa cctttatgta ttggtttgac acttttgagc    811 tttaaaaaaa aaaaaaaa                                                   829

<210> SEQ ID NO 12
<211> LENGTH: 197
<212> TYPE: PRT
<213> ORGANISM: Daucus carota

<400> SEQUENCE: 12

Gly Pro Val Pro Leu Phe Phe Pro Gln Leu Thr Lys Leu Thr Cys Leu
 1               5                  10                  15

Asp Leu Ser Phe Asn Lys Leu Leu Gly Val Ile Pro Pro Gln Leu Ser
            20                  25                  30

Thr Leu Pro Asn Leu Lys Ala Leu His Leu Glu Arg Asn Glu Leu Thr
        35                  40                  45

Gly Glu Ile Pro Asp Ile Phe Gly Asn Phe Ala Gly Ser Pro Asp Ile
    50                  55                  60

Tyr Leu Ser His Asn Gln Leu Thr Gly Phe Val Pro Lys Thr Phe Ala
65                  70                  75                  80

Arg Ala Asp Pro Ile Arg Leu Asp Phe Ser Gly Asn Arg Leu Glu Gly
                85                  90                  95

Asp Ile Ser Phe Leu Phe Gly Pro Lys Lys Arg Leu Glu Met Leu Asp
            100                 105                 110

Phe Ser Gly Asn Val Leu Ser Phe Asn Phe Ser Arg Val Gln Glu Phe
        115                 120                 125

Pro Pro Ser Leu Thr Tyr Leu Asp Leu Asn His Asn Gln Ile Ser Gly
    130                 135                 140

Ser Leu Ser Ser Glu Leu Ala Lys Leu Asp Leu Gln Thr Phe Asn Val
145                 150                 155                 160
```

```
                              -continued

Ser Asp Asn Asn Leu Cys Gly Lys Ile Pro Thr Gly Gly Asn Leu Gln
                165             170             175

Arg Phe Asp Arg Thr Ala Tyr Leu His Asn Ser Cys Leu Cys Gly Ala
                180             185             190

Pro Leu Pro Glu Cys
            195
```

CARROT ANTIFREEZE POLYPEPTIDES

TECHNICAL FIELD OF THE INVENTION

The invention relates to anti-freeze polypeptides (AFPs) and food product containing AFPs.

BACKGROUND TO THE INVENTION

Anti-freeze polypeptides (AFPs) have been suggested for improving the freezing tolerance of foodstuffs.

For the purpose of the invention, the term AFP has the meaning as well-known in the art, namely those proteins which inhibit the growth of ice-crystals. See for example U.S. Pat. No. 5,111,792.

WO 90/13571 discloses, antifreeze peptides produced chemically or by recombinant DNA techniques from slants. The AFPs can suitably be used in food-products such as ice-cream. Example 3B shows modified ice-crystal shapes if a water-ice mixture is frozen into a film in combination with 0.01 wt % of AFP.

WO 92/22581 discloses AFPs from plants which can be used for controlling ice crystal shape in ice-cream. This document also describes a process for extracting a polypeptide composition from intercellular spaces of plants by infiltrating leaves with an extraction medium without rupturing the plant cells.

WO 94/03617 discloses the production of AFPs from yeast and their possible use in ice-cream. WO 96/11586 describes fish AFPs produced by microbes.

Up till now, however the use of AFPs has not been applied to commercially available consumer products. One reason for this are the high costs and complicated process for obtaining AFPs. Another problem is that sources of the AFPs are either difficult to obtain in sufficient quantities (e.g. fish containing AFPs) or are not directly suitable for use in food products.

The present invention aims to provide novel antifreeze polypeptides which have the advantage that they can easily be obtained from an abundant natural source and which provide good properties to products in which they are used.

It has been found that antifreeze polypeptides which possess good recrystallisation inhibition properties can be obtained from carrots. In particular it has been found that antifreeze polypeptides obtained from carrots show markedly better properties as compared to polypeptides isolated from other root vegetables. In particular the antifreeze polypeptides of the invention are capable of providing good recrystallisation inhibition properties without significantly changing the crystal shape of the ice-crystals, therewith possible leading to more favourable properties e.g. soft ice-cream.

Applicants have found that the effective antifreeze polypeptides from carrots are generally characterised by an apparent Molecular Weight on SDS-PAGE of 36 kDa. Accordingly in a first aspect the invention relates to anti-freeze polypeptides which can be obtained from carrots and which have an apparent molecular weight on SDS-PAGE of 36 kDa.

In this context it will be clear to the skilled person that due to variation e.g. in SDS PAGE, the apparent molecular weight can only be determined with some variation in the results. For the purpose of the invention these variations e.g. from 30 to 40 kDa or from 34 to 39 kDa are also embraced within the scope of the term "apparent Molecular Weight of 36 kDa".

Applicants also have found that the effective anti-freeze polypeptides according to the invention comprise fragments having an amino acid sequence as represented in the examples.

Accordingly in a second aspect the invention relates to polypeptides comprising one or more fragments (A–E) having an amino add sequence as follows:

SEQ ID NOS. 1–5, respectively, in order of appearance.
(A) LEU-PRC-ASN-LEU-PHE-GLY-LYS
(B) ILE-PRO-GLU-GLU-ILE-SER-ALA-LEU-LYS
(C) LEU-THR-X-LEU-ASP-LEU-SER-PHE-ASN-LYS
(D) SER-LEU-ARG-LEU-SER-SER-THR-SER-LEU-SER-GLY-PRO-VAL-PRO-LEU-PHE-PHE-PRO-GLN-LEU-X-LYS
(E) X-X-GLU-VAL-ILE-PRO-X-GLN-LEU-SER-THR-LEU-PRO-ASN-LEU-LYS Preferably the AFPs of the invention comprise all of the partial sequences (A–E).

The complete amino acid sequence of the preferred AFP of the invention is represented below. Accordingly, in a third aspect the invention relates to an anti-freeze protein having an amino acid sequence as shown in Listing 1:

```
         ATGAATATTGAATCATCTTTCTGCCCTATTTTGTGCATATGCATGATTTTCCTCTGCCTT
      13 -------+---------+---------+---------+---------+---------+--    72
    a    M  N  I  E  S  S  F  C  P  I  L  C  I  C  M  I  F  L  C  L    -

CCAAACCTCTCTGCATCACAAAGATGCAACAACAACGACAAGCAAGCTTTACTCCAAATC
      73 -------+---------+---------+---------+---------+---------+--   132
    a    P  N  L  S  A  S  Q  R  C  N  N  N  D  K  Q  A  L  L  Q  I    -

AAAACAGCCTTGAAAAACCCCACCATTACAGACTCATGGGTGTCAGACGACGATTGTTGT
     133 -------+---------+---------+---------+---------+---------+--   192
    a    K  T  A  L  K  N  P  T  I  T  D  S  N  V  S  D  D  D  C  C    -

GGTTGGGACCTAGTCGAATGTGACGAAACCAGCAACCGCATAATTTCCCTCATAATTCAA
     193 -------+---------+---------+---------+---------+---------+--   252
    a    G  W  D  L  V  E  C  D  E  T  S  N  R  I  I  S  L  I  I  Q    -

GACGACGAAGCTCTCACCGGCCAAATCCCACCTCAGGTGGGAGACCTACCATACCTCCAA
     253 -------+---------+---------+---------+---------+---------+--   312
    a    D  D  E  A  L  T  G  Q  I  P  P  Q  V  G  D  L  P  Y  L  Q    -

GCCTTATGGTTCCGTAAACTCCCCAATCTTTTCGGAAAAATCCCAGAAGAAATTTCTGCA
```

```
                                                                                  372
313 --------+---------+---------+---------+---------+---------+--
a       A  L  W  F  R  K  L  P  N  L  F  G  K  I  P  E  E  I  S  A     -

CTCAAAGACCTAAAATCCCTCAGACTCAGCTCGACCAGTCTCAGTGGCCCTGTCCCTTTA
373 --------+---------+---------+---------+---------+---------+--         432
a       L  K  D  L  K  S  L  R  L  S  S  T  S  L  S  G  P  V  P  L     -

TTCTTCCCTCAGCTTACGAAACTAACTTGTTTAGACTTATCGTTTAACAAACTTTTGGGT
433 --------+---------+---------+---------+---------+---------+--         492
a       F  F  P  Q  L  T  K  L  T  C  L  D  L  S  F  N  K  L  L  G     -

GTAATCCCTCCTCAGCTTTCCACTCTTCCGAACCTTAAAGCCCTGCACTTAGAACGTAAC
493 --------+---------+---------+---------+---------+---------+--         552
a       V  I  P  P  Q  L  S  T  L  P  N  L  K  A  L  H  L  E  R  N     -

GAACTCACCGGTGAAATCCCCGATATCTTTGGGAATTTTGCTGGATCCCCGGACATATAT
553 --------+---------+---------+---------+---------+---------+--         612
a       E  L  T  G  E  I  P  D  I  F  G  N  F  A  G  S  P  D  I  Y     -

CTTTCGCATAACCAGCTCACCGGGTTTGTTCCCAAAACTTTTGCTAGAGCAGATCCAATT
613 --------+---------+---------+---------+---------+---------+--         672
a       L  S  H  N  Q  L  T  G  F  V  P  K  T  F  A  R  A  D  P  I     -

AGGCTCGACTTCTCAGGGAACAGACTAGAAGGTGATATTTCATTCTTGTTTGGGCCTAAA
673 --------+---------+---------+---------+---------+---------+--         732
a       R  L  D  F  S  G  N  R  L  E  G  D  I  S  F  L  F  G  P  K     -

AAACGCTTGGAAATGCTAGATTTTTCAGGAAACGTGCTTAGTTTCAATTTCTCCAGGGTG
733 --------+---------+---------+---------+---------+---------+--         792
a       K  R  L  E  M  L  D  F  S  G  N  V  L  S  F  N  F  S  R  V     -

CAGGAGTTTCCACCCTCTTTGACATACTTAGACTTGAACCATAACCAGATCAGCGGAAGT
793 --------+---------+---------+---------+---------+---------+--         852
a       Q  E  F  P  P  S  L  T  Y  L  D  L  N  H  N  Q  I  S  G  S     -

CTGTCGAGTGAATTGGCTAAATTGGACCTGCAGACATTTAACGTCAGTGATAATAATCTC
853 --------+---------+---------+---------+---------+---------+--         912
a       L  S  S  E  L  A  K  L  D  L  Q  T  F  N  V  S  D  N  N  L     -

TGCGGCAAGATTCCAACAGGGGGAAACCTCCAGAGATTCGACCGTACGGCCTATCTCCAC
913 --------+---------+---------+---------+---------+---------+--         972
a       C  G  K  I  P  T  G  G  N  L  Q  R  F  D  R  T  A  Y  L  H     -

AACAGTTGCTTGTGTGGTGCTCCATTGCCAGAATGCTAG
973 --------+---------+---------+---------+-                              1011
a       N  S  C  L  C  G  A  P  L  P  E  C  +                          -
```

SEQ ID NOS. 6 & 7

Listing 1

Also embraced within the invention are isoforms and derivatives of the above mentioned polypeptides which still possess the antifreeze properties. Preferable the derivatives show at least 75% homology with the polypeptide of Listing 1 or the polypeptide comprising the partial sequences (A–E) more preferred more than 85%, most preferred more than 95%. For the purpose of the invention the term derivative also embraces modified polypeptides which still possess the antifreeze properties, for example glycosylated forms of the above polypeptides.

Also embraced within the invention are nucleotide sequences encoding the amino acids as described above. In particular the invention relates to nucleotide sequences of Listing 1 and alleles thereof.

Also embraced within the invention are nucleotide fragments derived from the coding region that are capable of hybridizing to related genes that code for anti-freeze peptides.

Although the proteins of the invention can easily directly be isolated from carrots, also genetic manipulation techniques may be used to produce the proteins described in the invention.

An appropriate host cell or organism would be transformed by a gene construct that encodes the desired polypeptide. The nucleotide sequence coding for the polypeptide can be inserted into a suitable expression vector containing the necessary elements for transcription and translation and in a manner that they will be expressed under appropriate conditions (eg in proper orientation and correct reading frame and with appropriate targeting and expression sequences). The methods required to construct these expression vectors are well known to those skilled in the art.

A number of expression systems may be utilised to express the polypeptide coding sequence. These include, but are not limited to, bacteria, yeast, insect cell systems, plant cell culture systems and plants all transformed with the appropriate expression vectors. Yeast, plants and plant culture systems are preferred in this context.

A wide variety of plants and plant cell systems can be transformed with the nucleic acid constructs of the polypeptides. Preferred embodiments would include, but are not limited to, maize, tomato, tobacco, carrots, strawberries, rape seed and sugar beet.

One preferred embodiment of the invention relates to the use of AFPs of the invention for increasing the frost tolerance of plants. This case for example be done by the above method whereby the plants are transformed to ensure.

(increased) production of the AFPs of the invention, therewith increasing the frost tolerance of said plants.

The invention also relates to antibodies which specifically bind an (epitope of the) polypeptides of the invention. Also embraced are polypeptides which are immunologically related to the polypeptides as determined by its cross reactivity with an antibody raised against the above polypeptides.

Based on the above information it is also possible to genetically modify other natural sources such that they produce the advantageous AFPs as identified here-above.

Preferably those AFPs are chosen which have significant ice-recrystallisation inhibition properties. A suitable test for determining the recrystallisation inhibition properties is indicated in example I. Also preferably AFPs in accordance to the invention provide a ice particle size in the frozen product (mean crystal length) upon recrystallisation of less than 50 $\mu$M, more preferred from 5 to 40 $\mu$m.

The AFPs can conveniently be used in several products, preferably in food products which are frozen or intended to be frozen. Carrots which comprise the AFP at naturally occuring levels are not embraced within the scope of the invention. However, food product containing (parts) of carrots are embraced within this term. Also embraced are carrots which have been transformed to over express the AFP of the invention i.e. which contain the AFP at significantly higher levels than non-transformed carrots.

Examples of such food products are: frozen food products such as vegetables, sauces, soups, snacks, frozen confectionery products such as ice-cream or water-ice, dairy products etc.

The preferred products wherein the AFPs are used are or frozen vegetables or frozen confectionery products such as ice-cream or water-ice. Preferably the level of AFPs is from 0.00001 to 0.5 wt % based on the final product.

If dry-mixes or concentrates are used, the concentration may be higher in order to ensure that the level in the final frozen product is within the above ranges. Surprisingly it has been found that compositions of the invention can contain very low amounts of AFPs while still being of good quality.

Preferred levels of AFP are from 0.00001 to 0.5 wt %, more preferred 0.00005 to 0.3 wt %, most preferred 0.0001 to 0.2 wt %.

For the purpose of the invention it is not necessary to add the AFP in purified form to the food product. Also possible is to add a composition comprising AFPs e.g. an extract of the natural material which produces the AFP.

Also it is possible to modify the food product such that the AFP is produced in situ e.g. by adding genetically modified micro-organisms which are capable of producing the AFP in the food product, or even to genetically modify the food product (e.g. the vegetable) such that (the vegetable) in itself it is capable of producing the AFP in situ.

For the purpose of the invention the term frozen confectionery product includes milk containing frozen confections such as ice-cream, frozen yoghurt, sherbet, sorbet, ice milk and frozen custard, water-ices, granites and frozen fruit purees.

Preferably a the level of solids in the frozen confection (e.g. sugar, fat, flavouring etc) is more than 3 wt %, more preferred from 10 to 70 wt, for example 40 to 70 wt %.

Frozen confectionery products according to the invention can be produced by any method suitable for the production of frozen confectionery. Especially preferably however all the ingredients of the formulation are fully mixed before the freezing process starts.

EXAMPLES

Example I

Carrots (Daucus carota cv Autumn King) were grown in individual pots. When plants were approximately twelve weeks old, they were transferred to a cold room and held at 4° C. in constant light during 4 weeks for cold-acclimation. Plants were watered three times a week.

Fresh tissue of the carrots were ground with a pestle and mortar (cooled to 4° C.) in an equal volume buffer A (10 mM EDTA, 20 mM Ascorbic acid, buffered with Tris to pH 7.4) held on ice. The homogenates were filtered through one layer of muslin and kept on ice prior to further use.

As a comparison several other root-plants were grown and homogenates prepared from the roots as above.

Anti-freeze activity was measured using a modified "splat assay" (Knight et al, 1986). 2.5 $\mu$l of the solution under investigation in 30% (w/w) sucrose was transferred onto a clean, appropriately labelled, 16 mm circular coverslip. A second coverslip was placed on top of the drop of solution and the sandwich pressed together between finger and thumb. The sandwich was dropped into a bath of hexane held at −80° C. in a box of dry ice. When all sandwiches had been prepared, sandwiches were transferred from the −80° C. hexane bath to the viewing chamber containing hexane held at −6° C. using forceps pre-cooled in the dry ice. Upon transfer to −6° C., sandwiches could be seen to change from a transparent to an opaque appearance. Images were recorded by video camera and grabbed into an image analysis system (LUCIA, Nikon) using a 20× objective. Images of each splat were recorded at time=0 and again after 30–60 minutes. The size of the ice-crystals in both assays was compared. If the size at 30–60 minutes is similar or only moderately increased (say less than 20% increased, more preferred less than 10% increased, most preferred less than 5% increased) compared to the size at t=0, this is an indication of good ice-crystal recrystallisation inhibition properties.

Results: from the sandwich splat assay test it appeared that samples from carrot roots, carrot stem and carrot leaves possess significant ice-recrystallisation inhibition properties, whereby the roots and leaves are most active. As a comparison a sample of non-acclimated carrot roots was tested, which showed significant less activity. For the following examples root tissue was used for further testing on carrots.

As a comparison several other vegetable roots were investigated by means of the sandwich splat assay test in 30% sucrose. Among these vegetables were turnip, kale, brussels sprout, wintergreen cabbage, rape, pak choi, parsnip and strawberry. None of these sources of material provided significant ice-recrystallisation inhibition activity.

Example II

Carrot root tissue was homogenized in three volumes (w/v) buffer (20 mM ascorbic acid, 10 mM EDTA, 50 mM Tris/HCL, pH 7.2) in a pre-cooled pestle and mortar and filtered through one layer of muslin. The filtrate was centrifuged at 6,000 g, ten minutes at 4° C.; the supernatant was collected and centrifuged at 100,000 g for 1 hour at 4° C. The 100,000 g supernatant from this step is termed the soluble fraction and the pellet the microsomal fraction.

The supernatant was applied to a 30 ml fast flow Q Sepharose (Pharmacia) colum pre-equilibrated in 50 mM Tris/HCL pH 7.4 at a flow rate of 5 ml/min supplied by a HiLoad pump P-50 controlled by a Gradifrac low pressure chromatography system (Pharmacia) at 4° C. and the eluate monitored at OD 280 by a UV monitor (Monitor UV1, Pharmacia) recorded on a chart recorder (REC 102, Pharmacia). 5 ml fractions were collected. The column was washed with 50 mM Tris/HCL pH 7.4 at the same flow rate until the OD 280 returned to zero. A 150 ml gradient of 0–0.4 M NaCl in Tris/HCL pH 7.4 was then applied followed by a 2 M NaCl column wash. Eluate fractions were subjected to the splat assay as in example I.

Fractions containing anti-freeze activity as evidenced by recrystallisation inhibition were pooled and concentrated using polyethylene glycol as follows: the fractions were transferred in 10 kDa cut off dialysis tubing (Sigma) which had been washed in tap water, boiled in 50 mM EDTA pH 7.5 for 10 minutes and rinsed in milli Q water. The dialysis tubing containing the sample to be concentrated was covered with solid polyethylene glycol compound Mol. Wt. 15,000–20,000 (Sigma) and incubated at 4° C. for up to 4 hours or until the sample volume inside the dialysis tubing had reduced up to 10 fold.

The pooled concentrate from the Q sepharose column was applied either to a phenyl Sepharose column, a SMART superdex 75 gel permeation column or an FPLC superdex 75 gel permeation column.

Carrot root anti-freeze proteins were purified by gel permeation chromatography as follows:

20 µl aliquots of sample were applied to a SMART superdex 75 column (Pharmacia) pre-equilibrated in 50 mM Tris/HCl pH7.4 containing 0.15M NaCl (Buffer E) at a flow rate of 40 µl/min and components separated by gel permeation at the same flow rate in equilibration buffer. The eluate was monitored at OD 280 and OD 215. 80 µl fractions were collected between 0.85 and 0.89 ml, 40 µl fractions between 0.89 and 1.24 ml and 100 µl fractions between 1.24 and 3.0 ml. The void volume (Vo) of the column was 0.91 ml as determined by the retention volume of a solution of Blue Dextran. The superdex column was calibrated by application of 10 µl of a solution containing 5 mg/ml BSA (Mr 66 kDa, retention (Ve)=1.02 ml), 3 mg/ml Carbonic anhydrase (Mr, 29 kDa, Ve=1.22 ml), 2 mg/ml Cytochrome C (Mr 12.4 kDa, Ve=1.41 ml) and 2 mg/ml Aprotinin (Mr 6.5 kDa, Ve=1.59 ml) and a standard curve plotted of Ve/Vo against log Mr. Fractions containing anti-freeze activity were identified by the splat assays as described in Example I, with an activity peak that showed a retention volume of 1.16 ml and an apparent molecular weight of 40 kDa. These measurement confirmed that the 36 kDa band from cold acclimatised carrots was an anti-freeze peptide.

SDS-PAGE was carried out according to Laemmli (1970) using the Biorad mini system. Samples to be analyzed by SDS-PAGE were dissolved in SDS-PAGE sample buffer (Laemmli 1970), heated for 5 minutes at 100° C. on a dry heating block (Techne) and centrifuged for 3 minutes at 10,000 g at room temperature. Samples (10–50 µl) were applied to mini-gels (Biorad, 0.75,1.0 or 1.5 mm thickness, 10,12,15% acrylamide or 0–20% gradient acrylamide {prepoured from Biorad}) and electrophoretically separated. Separated polypeptides were fixed and stained in the gel either with Coomassie blue (0.1% {w/v} Coomassie Brilliant Blue in acetic acid/methanol/miliQ water {5:4:31, by vol}) or silver stained using the Biorad silver stain kit according to the manufacturer's instructions. Gels were dried between two sheets of Gelair cellophane in a Biorad gelair dryer according to the manufacturer's instructions. Sigma high and low range molecular weight marker kits were used according to the manufacturer's instructions for determination of apparent $M_r$ on SDS-PAGE.

The ion exchange chromatography was carried out with cold acclimatised carrot root and non-cold acclimatised carrot root. The resulting gel SDS-PAGE gels showed the presence of a 36 kDa band in the cold acclimatised sample. This band was much less abundant in the non-cold acclimatised root. This 36 kDa band was hence attributed to anti-freeze activity.

Example III

For protein sequencing, the 36 kDa carrot root protein was purified as described in the previous example and then to ensure further purification the sample to be sequenced was excised from the SDS PAGE gel and then proteolytically digested in situ in the polyacrylamide gel slice.

Preparations of largely pure 36 kDa protein, that still had some minor contaminating proteins, were loaded onto a 12% polyacrylamide gel. Three lanes each with 2 µg of protein were loaded and electrophoresed in the gel until the dye front reached the bottom of the gel. The gel was then stained in 0.2% uocmassie brilliant blue (w/v), 30% methanol (v/v), 1% acetic acid (v/v) for 20 minutes and then destain with 30% methanol until the protein bands could be visualised. The 36 kDa band was identified by comparison with molecular weight markers loaded into adjacent lanes and the band from each lane was excised with a scalpel blade, taking care to exclude contaminating bands.

The gel slices were transferred to a clean eppendorf tube and washed twice with 0.5 ml of 50% acetonitrile (v/v), 100 mM Tris/Cl, pH 8.5. The washing removed some of the uocmassie stain and also partially dehydrated the gel slices. The gel slices were then removed from the tube and subjected to air drying on the laboratory bench until they had shrunk significantly and started to curl up. They were then transferred back to the eppendorf and rehydrated with firstly, 10 µl of 100 mM Tris/Cl, pH 8.5 containing 1 µg of endoproteinase Lys C (Boehringer Mannheim). This is a proteinase that specifically cleaves polypeptide chains on the carboxy terminal side of lysine residues. Further Tris buffet was added to the gel slices until they were fully rehydrated and they were then incubated at 37° C. for 16 hours.

After incubation 1 µl of trifluoroacetic acid was added to the tube to stop the reaction and then the gel slices were washed twice with 0.3 ml of 60% acetonitrile (v/v), 0.1% TFA (v/v) at 30° C. for 30 minutes. This was to again partially dehydrate the gel slices causing them to shrink and elute the peptides that had been generated. The supernatant was transferred to another clean eppendorf tube and then dried in a centrifugal evaporator for 2 hours until the sample was near dryness and resuspended to a volume of 0.1 ml with 0.1% TFA.

The peptides were then separated by reversed phase HPLC on a Smart micropurification system (Pharmacia). The peptide digest was loaded onto a C18 column (2.1×100 mm) equilibrated in 0.1% TFA (Solvent A) at a flow rate of 0.1 ml min. The column was then eluted with a gradient of 0–70% of Solvent B (90% acetonitrile v/v, 0.085% TFA v/v) over 70 minutes at the same flow rate. The optical density was monitored at 214 nm and individual peptide peaks were collected in the fraction collector by manual stepping. Polypeptides were sequenced by loading onto a model 492 Perkin Elmer protein sequencer using the liquid phase chemistry cycles as recommended by the manufacturer.

Several polypeptide fragments (A–E) were analyzed in the 36 kDa band and had sequences substantially homologous to:

SEQ ID NOS 1–5, respectively, in order of appearance (A) LEU-PRO-ASN-LEU-PHE-GLY-LYS
(B) ILE-PRO-GLU-GLU-ILE-SER-ALA-LEU-LYS
(C) LEU-THR-X-LEU-ASP-LEU-SER-PHE-ASN-LYS
(D) SER-LEU-ARG-LEU-SER-SER-THR-SER-LEU-SER-GLY-PRO-VAL-PRO-LEU-PHE-PHE-PRO-GLN-LEU-X-LYS
(E) X-X-GLY-VAL-ILE-PRO-X-GLN-LEU-SER-THR-LEU-PRO-ASN-LEU-LYS Example IV-a Carrot Cell Culture A carrot cell suspension culture line (NOR) was obtained from the Department of Biochemistry and Molecular Biology, University of Leeds. The culture was maintained by subculturing 10 ml of the culture into 90 ml of fresh Murashige and Skoog medium (Sigma) containing 25 g/l sucrose and 1 mg/l 2,4-D every seven days. Cultures were incubated in an orbital shaking incubator at 150 rpm at 25° C. in the dark.

The NOR culture was cold treated as follows:

NOR cultures were transferred to 4° C. after 4d and 7d of growth at 25° C. Cultures were harvested at t=0, t=7d and t=14d. In addition to harvesting, the packed cell volume (PCV) was determined for each culture at each time point.

The media samples from NOR suspension cultures were analyzed as follows. Approximately 1/10th of the volume of a frozen aliquot of conditioned suspension culture medium was allowed to defrost. The defrosted (freeze concentrated) portion was removed and tested for activity by sandwich splat assays as described in Example I. Medium from cold acclimated cultures was found to contain significantly more activity than medium from non-cold acclimated cultures.

The cold acclimated NOR carrot medium was buffered by addition of 100 μl of 1M Tris/HCl pH 7.4. Purification of activity was then performed by ion exchange and gel permeation chromatography using a method based on that in Example II: the buffered medium was applied to a 1 ml Q Sepharose column (Pharmacia) at a flow rate of 1 ml/min and bound molecules eluted with 3 ml aliquots of 500 mM Tris/HCl pH 7.4 containing concentrations of NaCl starting at 0.1 M and increasing to 0.5 M in 0.1 M steps. 1 ml fractions were collected and tested for activity as in Example I.

The antifreeze activity in the active ion exchange fractions was purified by gel permeation chromatography as follows. The active fraction from above was acetone precipitated and the pellet resuspended in 50 μl 50 mM Tris/HCl+0.15 M NaCl, pH 7.2. This was then centrifuged at 10.000 g for 10 minutes, and 20 μl loaded onto a Superdex 75 gel permeation column on the Pharmacia SMART system. The flow rate was 40 μl/min and the mobile phase was 50 mM Tris/HCl+0.15M NaCl, pH 7.2. 80 μl fractions were collected and splatted. Activity was detected in fractions corresponding to a retention of 1.16 ml.

Further isolation of the active proteins can be done by SDS PAGE analysis in line with Example II.

Example IV-b Carrot Root Culture

Carrot root cultures were initiated as follows.

For each individual culture 10 surface sterilised *Daucus carote* cv Autumn King seeds were placed into 100 ml MS medium containing 25 g/L sucrose and 0.5 g/L MES in sterile 250 ml Erlenmyer flasks. Seeds were germinated by shaking at 150 rpm in the dark at 25° C. for 3 weeks. Leaves and shoots were then aseptically removed. The roots were replaced into 100 ml fresh medium and incubated with shaking for a further 2 weeks.

Homogenates were prepared from cold treated and non-cold treated root cultures as follows. Fast frozen roots were ground up 3× in liquid nitrogen in a cold mortar and pestle then transferred to a further chilled mortar and pestle and ground up with 0.5× volume of ice-cold 50 mM Tris.HCl+10 mM EDTA pH 7.4 containing 30% w/w sucrose. Homogenates were centrifuged at 10.000 g for 10 minutes at 4° C. and the supernatant tested for activity as in Example I.

Significantly more activity was detected in cold treated root cultures than in non-cold treated root cultures.

Example V Preparation of Ice-cream

Root extract from cold acclimatised carrot roots was prepared by scrubbing freshly pulled cold acclimatised (as in example I) carrots in cold water. The tops are removed and the juice extracted employing a domestic juice extractor (Russell Hobbs, model no 9915). The juice was frozen in 1 liter blocks and stored a −20° C. prior to collection for use in ice cream trials. The carrot AFP juice was added to the following ice cream formulation:

| INGREDIENT | parts by weight |
|---|---|
| Skimmed Milk Powder | 10.000 |
| Sucrose | 13.000 |
| MD40 | 4.000 |
| Locust Bean Gum | 0.144 |
| Genulacta L100 | 0.016 |
| MGP | 0.300 |
| Butteroil | 8.000 |
| Vanillin | 0.012 |
| Water | 64.528 |
| Carrot Extract (from cold acclimated carrots containing 1–10 mg AFP per kg) | 4.472 |

Ice-cream was prepared by freezing the above formulation and aeration to 106% overrun.

Measurements were made on fresh sample and on samples which had been abused by storage at −10° C. for a period of 10 days. As a comparison a sample without carrot extract was measured in the same way. The measurements were done as follows:

Samples were equilibrated at −18° C. in a Prolan Environmental cabinet for approximately 12 hours. Three samples were chosen representatively from each batch of ice cream and a slide was prepared from each in a Cryostat temperature control cabinet by smearing a thin layer of ice cream from the centre of each block onto a microscopic slide. A single drop of white spirit was applied to the slide and a cover slip was then applied. Each slide, in turn, was then transferred to a temperature controlled microscope stage (Leit LaborLux S, Leica x10 objective, temperature −18° C.). Images of ice-crystals (about 400 individual ice-crystals) were collected and relayed through a video camera (Sanyo CCD) to an image storage and analysis system (LEICA Q520MC).

The stored ice crystal images were highlighted manually by drawing around the perimeter which then highlights the whole crystal. Images of the highlighted crystals were then measured using the image analysis software which counts the number of pixels required to complete the longest straight line (length), shortest straight line (breadth), the aspect ratio (length/breadth). The data for each individual ice crystal of a batch of ice cream was imported into a spreadsheet where analysis of the data set was carried out to find the mean, and standard deviation.

The ice Cream Hardness Measurements were carried out using a Hounsfield H10KM Universal Tester, a Hounsfield 100N Load Cell and a 10 cm Cylindrical Stainless steel probe. The ice-cream samples were prepared by 16 Hour incubation of 486 ml ice cream blocks in a Prolan Temperature Control Cabinet set at −13° C.

The ice cream block was removed from Prolan temperature control cabinet and placed the Hounsfield H10KM Universal Tester. The 10 cm cylindrical probe was pushed into the ice cream block at a constant rate of 400 mm/min to a depth of 20 mm. The maximum force recorded during the compression was used and expressed as the ice cream Hardness. If cracking or brittle fracture of the sample was observed this was indicated in the right hand column.

The following results were obtained

| | Ice Crystal Size Parameters | | | | Material Properties | |
|---|---|---|---|---|---|---|
| Sample | Mean Crystal Length/ um | Mean Crystal Breadth/ um | Mean Crystal Shape Factor/ - | Mean Crystal Aspect Ratio/ - | Hard- ness/ N | Brittle Fracture observation |
| Carrot AFP- fresh | 26.79 ± 1.3 | 19.00 ± 0.9 | 1.15 ± 0.013 | 1.43 ± 0.024 | 40.8 | Yes |
| Carrot AFP- Abused | 33.48 ± 1.3 | 24.61 ± 0.9 | 1.13 ± 0.013 | 1.37 ± 0.020 | 59.9 | Yes |
| Cont.- Fresh | 33.67 ± 1.1 | 24.79 ± 0.8 | 1.12 ± 0.008 | 1.38 ± 0.018 | 27.3 | Yes |
| Cont.- Abused | 61.77 ± 2.7 | 46.54 ± 2.0 | 1.11 ± 0.010 | 1.37 ± 0.020 | 32.7 | Yes |

This proves that carrot AFP has good ice recrystallisation inhibition properties.

Example VI

The peptide sequences shown in Example III were analyzed as to their suitability for degenerate oligonucleotide primer design. Part of Peptide D SEQ ID NO: 8 (GLY-PRO-VAL-PRO-LEU-PHE-PHE-PRO) was chosen and the primer cp3 SEQ ID NO:9 (GGI CCI GTI CCI YTI TTY TTY CC, where I=inosine and Y=C or T) was synthesized (Genosys).

First strand cDNA was prepared from 5 $\mu$g cold acclimated (1 month as in example I) carrot root RNA using Superscript Reverse Transcriptase (Stratagene) and an oligonucleotide primer OG1 SEQ ID NO: 10 (GAGAGAGGATCCTCGAG(T)$^{15}$) according to the manufacturer's instructions. 1% of the first strand cDNA reaction was used as template, together with cp3 and OG1 primers, in subsequent PCR. The reactions were carried out in a thermal cycler using Taq DNA polymerase (Gibco BRL) for 30 cycles (1 minute at 94° C., 1 minute at 50° C. and 1 minute at 72° C.) according to the manufacturer's instructions. All primers were used at a concentration of 1 $\mu$M. The resulting ~800 bp PCR product was gel purified and cloned into the pTAg vector (R&D Systems) according to the manufacturer's instructions. The cloned cp3 PCR product was sequenced using the dideoxy sequencing method employed by the Sequenase kit (USB). The cp3 nucleotide sequence and deduced amino acid sequence were substantially similar to:

SEQ ID NOS. 11 & 12

```
                         Listing II

GGGCCGGTGCCGCTGTTCTTCCCTCAGCTTACGAAACTAACTTGTTTAGACTTATCGTTT
   1   ---------+---------+---------+---------+---------+---------+    60
 a       G  P  V  P  L  F  F  P  Q  L  T  K  L  T  C  L  D  L  S  F   -

AACAAACTTTTGGGTGTAATCCCTCCTCAGCTTTCCACTCTTCCGAACCTTAAAGCCCTG
  61   ---------+---------+---------+---------+---------+---------+   120
 a       N  K  L  L  G  V  I  P  P  Q  L  S  T  L  P  N  L  K  A  L   -

CACTTAGAACGTAACGAACTCACCGGTGAAATCCCCGATATCTTTGGGAATTTTGCTGGA
 121   ---------+---------+---------+---------+---------+---------+   180
 a       H  L  E  R  N  E  L  T  G  E  I  P  D  I  F  G  N  F  A  G   -

TCCCCGGACATATATCTTTCGCATAACCAGCTCACCGGGTTTGTTCCCAAAACTTTTGCT
 191   ---------+---------+---------+---------+---------+---------+   240
 a       S  P  D  I  Y  L  S  H  N  Q  L  T  G  F  V  P  K  T  F  A   -

AGAGCAGATCCAATTAGGCTCGACTTCTCAGGGAACAGACTAGAAGGTGATATTTCATTC
 241   ---------+---------+---------+---------+---------+---------+   300
 a       R  A  D  P  I  R  L  D  F  S  G  N  R  L  E  G  D  I  S  F   -

TTGTTTGGGCCTAAAAAACGCTTGGAAATGCTAGATTTTTCAGGAAACGTGCTTAGTTTC
 301   ---------+---------+---------+---------+---------+---------+   360
 a       L  F  G  P  K  K  R  L  E  M  L  D  F  S  G  N  V  L  S  F   -

AATTTCTCCAGGGTGCAGGAGTTTCCACCCTCTTTGACATACTTAGACTTGAACCATAAC
```

Listing II

```
              361 ---------+---------+---------+---------+---------+---------+  420
a                 N  F  S  R  V  Q  E  F  P  P  S  L  T  Y  L  D  L  N  H  N  -

CAGATCAGCGGAAGTCTGTCGAGTGAATTGGCTAAATTGGACCTGCAGACATTTAACGTC
              421 ---------+---------+---------+---------+---------+---------+  480
a                 Q  I  S  G  S  L  S  S  E  L  A  K  L  D  L  Q  T  F  N  V  -

AGTGATAATAATCTCTGCGGCAAGATTCCAACAGGGGGAAACCTCCAGAGATTCGACCGT
              481 ---------+---------+---------+---------+---------+---------+  540
a                 S  D  N  N  L  C  G  K  I  P  T  G  G  N  L  Q  R  F  D  R  -

ACGGCCTATCTCCACAACAGTTGCTTGTGTGGTGCTCCATTGCCAGAATGCTAGTTACCA
              541 ---------+---------+---------+---------+---------+---------+  600
a                 T  A  Y  L  H  N  S  C  L  C  G  A  P  L  P  E  C  +

TGCAAAATGTGCCTTAAGGTTATCTTTGTAATGAGATATATTATGCAGCTCAAGGCAGAG
              601 ---------+---------+---------+---------+---------+---------+  660

CAATAAGTTTTCCTAATTTGTTATAGTAAGATATTATTGTATTTCACAGAAAGTGTCTAC
              661 ---------+---------+---------+---------+---------+---------+  720

TAGGATTCGTAATATATTATAATTGCTCATAATTGTATCTGTTTAATCTGTAATCCAAAA
              721 ---------+---------+---------+---------+---------+---------+  780

ACCTTTATGTATTGGTTTGACACTTTTGAGCTTTAAAAAAAAAAAAAAA
              781 ---------+---------+---------+---------+---------  829
```

In order to obtain the full coding region for the carrot AFP, a cDNA library was constructed. A poly (A)+ quick column (Stratagene) was used to purify mRNA from 500 µg CA (1 month) carrot total RNA, according to manufacturer's instructions. All resulting poly (A)+ RNA was used for cDNA synthesis and subsequent library construction using the lambda ZAP vector kit (Stratagene). 1×10[5] recombinant phage clones were screened by hybridization using the cp3 PCR product as a $^{32}$P labelled probe.

Positive plaques were screened to purity and phage-mids excised before the inserts were characterised by DNA sequence analysis. Two cDNA clones were sequenced to completion. Although the 5' and 3' untranslated regions contained some sequence variability, the coding regions were identical. The coding regions of the two cDNA clones were substantially similar to:

SEQ ID NOS. 6 & 7

Listing I

```
                  ATGAATATTGAATCATCTTTCTGCCCTATTTTGTGCATATGCATGATTTTCCTCTGCCTT
               13 -------+---------+---------+---------+---------+---------+--  72
a                 M  N  I  E  S  S  F  C  P  I  L  C  I  C  M  I  F  L  C  L  -

CCAAACCTCTCTGCATCACAAAGATGCAACAACAACGACAAGCAAGCTTTACTCCAAATC
               73 -------+---------+---------+---------+---------+---------+--  132
a                 P  N  L  S  A  S  Q  R  C  N  N  N  D  K  Q  A  L  L  Q  I  -

AAAACAGCCTTGAAAAACCCCACCATTACAGACTCATGGGTGTCAGACGACGATTGTTGT
              133 -------+---------+---------+---------+---------+---------+--  192
a                 K  T  A  L  K  N  P  T  I  T  D  S  W  V  S  D  D  D  C  C  -

GGTTGGGACCTAGTCGAATGTGACGAAACCAGCAACCGCATAATTTCCCTCATAATTCAA
              193 -------+---------+---------+---------+---------+---------+--  252
a                 G  W  D  L  V  E  C  D  E  T  S  N  R  I  I  S  L  I  I  Q  -

GACGCACGAAGCTCTCACCGGCCAAATCCCACCTAGGTGGGAGACCTACCATACCTCCAA
              253 -------+---------+---------+---------+---------+---------+--  312
a                 D  D  E  A  L  T  G  Q  I  P  P  Q  V  G  D  L  P  Y  L  Q  -

GCCTTATGGTTCCGTAAACTCCCCAATCTTTTCGGAAAAATCCCAGAAGAAATTTCTGCA
              313 -------+---------+---------+---------+---------+---------+--  372
a                 A  L  W  F  R  K  L  P  N  L  F  G  K  I  P  E  E  I  S  A  -

CTCAAAGACCTAAAATCCCTCAGACTCAGCTCGACCAGTCTCAGTGGCCCTGTCCCTTTA
              373 -------+---------+---------+---------+---------+---------+--  432
a                 L  K  D  L  K  S  L  R  L  S  S  T  S  L  S  G  P  V  P  L  -

TTCTTCCCTCAGCTTACGAAACTAACTTGTTTAGACTTATCGTTTAACAAACTTTTGGGT
              433 -------+---------+---------+---------+---------+---------+--  492
```

-continued

Listing I

```
a      F  F  P  Q  L  T  K  L  T  C  L  D  L  S  F  N  K  L  L  G       -

GTAATCCCTCCTCAGCTTTCCACTCTTCCGAACCTTAAAGCCCTGCACTTAGAACGTAAC
  493  -------+---------+---------+---------+---------+---------+--    552
a      V  I  P  P  Q  L  S  T  L  P  N  L  K  A  L  H  L  E  R  N       -

GAACTCACCGGTGAAATCCCCGATATCTTTGGGAATTTTGCTGGATCCCCGGACATATAT
  553  -------+---------+---------+---------+---------+---------+--    612
a      E  L  T  G  E  I  P  D  I  F  G  N  F  A  G  S  P  D  I  Y       -

CTTTCGCATAACCAGCTCACCGGGTTTGTTCCCAAAACTTTTGCTAGAGCAGATCCAATT
  613  -------+---------+---------+---------+---------+---------+--    672
a      L  S  H  N  Q  L  T  G  F  V  P  K  T  F  A  R  A  D  P  I       -

AGGCTCGACTTCTCAGGGAACAGACTAGAAGGTGATATTTCATTCTTGTTTGGGCCTAAA
  673  -------+---------+---------+---------+---------+---------+--    732
a      R  L  D  F  S  G  N  R  L  E  G  D  I  S  F  L  F  G  P  K       -

AAACGCTTGGAAATGCTAGATTTTTCAGGAAACGTGCTTAGTTTCAATTTCTCCAGGGTG
  733  -------+---------+---------+---------+---------+---------+--    792
a      K  R  L  E  M  L  D  F  S  G  N  V  L  S  F  N  F  S  R  V       -

CAGGAGTTTCCACCCTCTTTGACATACTTAGACTTGAACCATAACCAGATCAGCGGAAGT
  793  -------+---------+---------+---------+---------+---------+--    852
a      Q  E  F  P  P  S  L  T  Y  L  D  L  N  H  N  Q  I  S  G  S       -

CTGTCGAGTGAATTGGCTAAATTGGACCTGCAGACATTTAACGTCAGTGATAATAATCTC
  853  -------+---------+---------+---------+---------+---------+--    912
a      L  S  S  E  L  A  K  L  D  L  Q  T  F  N  V  S  D  N  N  L       -

TGCGGCAAGATTCCAACAGGGGGAAACCTCCAGAGATTCGACCGTACGGCCTATCTCCAC
  913  -------+---------+---------+---------+---------+---------+--    972
a      C  G  K  I  P  T  G  G  N  L  Q  R  F  D  R  T  A  Y  L  H       -

AACAGTTGCTTGTGTGGTGCTCCATTGCCAGAATGCTAG
  973  -------+---------+---------+----------+-                        1011
a      N  S  C  L  C  G  A  P  L  P  E  C  +                            -
```

Partial sequence analysis of 4 other clones also indicated that they contained the same coding region as the fully sequenced clones and thus all the positives from the library screen were likely to represent transcripts from the same gene. The existence of only one copy of the AFP gene in the carrot genome was further substantiated by the fact that Southern analysis of restriction enzyme digested carrot genomic DNA suggested that only one fragment hybridized to the probe.

Example VII

In order to prove that the carrot cDNA as shown in example VI represented an AFP, expression of the coding region was carried out as follows. One of the cDNAs was first cloned into an intermediate pUC plasmid vector (Messing, 1983) containing a double CaMV 35S promoter (Guerineau, J. F., Woolsten, S., Brooks, L., and Mollineaux, P. (1988)) expression cassette, and then into a binary vector, as described below. All enzymes used were supplied by Gibco BRL and used according to the manufacturer's instructions.

The pBluescript phagemid (Stratagene) containing the cDNA clone was digested with Xho I and the recessed 3' termini filled in using the Klenow fragment of DNA polymerase I. The cDNA fragment was then released from the vector by digestion with Eco RI. The Eco RI/blunt cDNA fragment was then cloned into the Eco RI/blunt digested intermediate pUC plasmid vector. The CaMV 35S-cDNA expression cassette was then subcloned as a partial Hind III fragment into Hind III-cut pBin 19 binary vector (Bevan 1984). The binary vector construct was then introduced into tobacco using Agrobacterium mediated transformation (as described in Draper, J., Scott, R., Armatage, P., and Walden, R. (1988)).

Transgenic tobacco callus was analyzed or expression of recrystallisation inhibition activity as soon as sufficient kanamycin resistant material was regenerated. Small scale protein extracts were made from several independent kanamycin resistant calli plus some wild type tobacco callus. Approximately 2 g tissue was ground up in 1–2 mls sucrose buffer (30% sucrose 50 mM Tris, 10 mM EDTA, 20 mM ascorbate, pH 7.2) using a mortar and pestle. The solution was centrifuged at 10,000×g for 2 minutes and the supernatant removed to a fresh tube. An aliquot of 3 μl of protein extract was tested for recrystallisation activity using the sucrose sandwich splat assay method of example I. All kanamycin resistant callus extracts tested demonstrated recrystallisation inhibition activity.

Stable transgenic tobacco plants expressing the carrot AFP have also been produced. Leaf extracts from wild-type and transgenic tobacco plants have been subjected to northern analysis using the AFP cDNA as a probe. The AFP message was only detectable in the transgenic tobacco plants. This suggests that the AFP message is stable in the greenhouse grown transgenic tobacco plants. When compared with the native carrot transcript, the tobacco AFP transcript appears to be slightly bigger. This discrepancy can be explained by the method of construction of the AFP expression cassette. Because the CaMV 35S polyadenylation signal is most 3' in the construct, it is likely that this signal is used in the transgenic AFP message, giving rise to a longer transcript. Leaf extracts from wild-type and transgenic tobacco plants have also been analyzed by western blotting using a carrot AFP antibody. A cross-reacting protein was only detected in the transgenic tobacco plants. Despite the difference in transcript size, the protein produced in tobacco appears to be the same size as the native carrot AFP.

The above data provides the proof that the protein purified from carrot and the corresponding cDNA represent an active AFP.

What is claimed is:

1. An isolated polypeptide having antifreeze activity which is obtained from carrots and which have an apparent molecular weight on sodium dodecyl sulfate polyacrylamide gel electrophoresis (SDS-PAGE) of 36 kDa.

2. A method of obtaining a polypeptide according to claim 1, comprising providing cold acclimatised carrot material containing said polypeptide, and purifying said polypeptide from a carrot.

3. A food product comprising a polypeptide according to claim 1 with the proviso that the food product is not a carrot containing the polypeptide at naturally occurring levels.

4. An isolated polypeptide having antifreeze activity comprising amino acid sequences SEQ ID NOS: 1,2,4,3 and 5 in the following order within the polypeptide:

(A) LEU-PRO-ASN-LEU-PHE-GLY-LYS (SEQ ID NO: 1)

(B) ILE-PRO-GLU-GLU-ILE-SER-ALA-LEU-LYS (SEQ ID NO: 2)

(D) SER-LEU-ARG-LEU-SER-SER-THR-SER-LEU-SER-GLY-PRO-VAL-PRO-LEU-PHE-PHE-PRO-GLN-LEU-X-LYS (SEQ ID NO: 4)

(C) LEU-THR-X-LEU-ASP-LEU-SER-PHE-ASN-LYS (SEQ ID NO: 3)

(E) X-X-GLY-VAL-ILE-PRO-X-GLN-LEU-SER-THR-LEU-PRO-ASN-LEU-LYS (SEQ ID NO: 5), wherein X is any amino acid.

5. A method of obtaining a polypeptide according to claim 4, comprising providing cold acclimatised carrot material containing said polypeptide, and purifying said polypeptide from the carrot material.

6. An isolated polypeptide having antifreeze activity that is specifically bound by an antibody which specifically binds to the polypeptide of claim 4.

7. A food product comprising a polypeptide of claim 4 with the proviso that the food product is not a carrot.

8. The food product of claim 7 being a frozen confectionery product or a frozen vegetable.

9. A method of producing a food product comprising an antifreeze polypeptide according to claim 4, comprising the step of adding to the food product a composition comprising said antifreeze polypeptide.

10. A food product comprising a polypeptide according to claim 4 with the proviso that the food product is not a carrot containing the polypeptide at naturally occurring levels.

11. A food product according to claim 10 wherein the food product is a frozen confectionery product or a frozen vegetable.

12. An isolated polypeptide having antifreeze activity comprising amino acid sequences (A)–(E) in the following order within the polypeptide:

(A) LEU-PRO-ASN-LEU-PHE-GLY-LYS (SEQ ID NO: 1) or an amino acid sequence having at least 85% identity thereto;

(B) ILE-PRO-GLU-GLU-ILE-SER-ALA-LEU-LYS (SEQ ID NO: 2) or an amino acid sequence having at least 85% identity thereto;

(D) SER-LEU-ARG-LEU-SER-SER-THR-SER-LEU-SER-GLY-PRO-VAL-PRO-LEU-PHE-PHE-PRO-GLN-LEU-X-LYS (SEQ ID NO: 4) or an amino acid sequence having at least 85% identity thereto;

(C) LEU-THR-X-LEU-ASP-LEU-SER-PHE-ASN-LYS (SEQ ID NO: 3) or an amino acid sequence having at least 85% identity thereto;

(E) X-X-GLY-VAL-ILE-PRO-X-GLN-LEU-SER-THR-LEU-PRO-ASN-LEU-LYS (SEQ ID NO: 5), or an amino acid sequence having at least 85% identity thereto;

wherein X is any amino acid.

13. An isolated polypeptide having antifreeze activity having an amino acid sequence as represented in SEQ ID NO: 7.

14. A food product comprising a polypeptide according to claim 13 wherein the food product is a frozen confectionery product or a frozen vegetable with the proviso that the food product is not a carrot.

15. An isolated polypeptide having antifreeze activity having an amino acid sequence having at least 95% identity to the amino acid sequence represented in SEQ ID No: 7.

16. A food product comprising a polypeptide according to claim 15 with the proviso that the food product is not a carrot containing the polypeptide at naturally occurring levels.

* * * * *